United States Patent [19]

Flender

[11] Patent Number: 5,179,086

[45] Date of Patent: Jan. 12, 1993

[54] TOPICAL OINTMENT

[75] Inventor: Gabriele Flender, Altenburgring 43, W-6991 Igersheim, Fed. Rep. of Germany

[73] Assignees: Wolfgang Weck, Bad Mergentheim; Gabriele Flender, Igersheim, both of Fed. Rep. of Germany

[21] Appl. No.: 671,740

[22] PCT Filed: Oct. 26, 1989

[86] PCT No.: PCT/EP89/01276

§ 371 Date: Apr. 30, 1991

§ 102(e) Date: Apr. 30, 1991

[87] PCT Pub. No.: WO90/04967

PCT Pub. Date: May 17, 1990

[30] Foreign Application Priority Data

Oct. 31, 1988 [DE] Fed. Rep. of Germany ....... 3836971

[51] Int. Cl.$^5$ ................................................ A61K 31/56
[52] U.S. Cl. ..................................... 514/182; 514/863
[58] Field of Search ................................. 514/182, 863

[56] References Cited

U.S. PATENT DOCUMENTS 4,743,597 5/1988 Javitt et al. ......................... 514/182

OTHER PUBLICATIONS

Balsam et al–Cosmetics, Science & Technology, 2nd ed, vol. 1, pp. 20, 21 & 48–52 (1972).
Chemical Abstracts 105:49069e (1986).

*Primary Examiner*—Leonard Schenkman
*Attorney, Agent, or Firm*—Spencer, Frank & Schneider

[57] ABSTRACT

This invention relates to topical ointments containing cholesterol for the treatment of dermatoses, in particular psoriasis.

7 Claims, No Drawings

TOPICAL OINTMENT

BACKGROUND OF THE INVENTION

The invention relates to a method of treating dermatoses and to a topical ointment for the treatment of dermatoses, in particular psoriasis.

Many kinds of ointments for the treatment of dermatological problems are known, which are applied to diseased sites on the skin. For the treatment of psoriasis and eczemas, ointments that contain corticosteroids or salicylic acid as the pharmaceutically active substances are used with preference. However, it has been found again and again that these ointments often lack the desired healing effect. Furthermore, in patients treated with topical media containing cortisone, serious side effects have been found, such as incurable aging of the skin (atrophy). Also encountered frequently are skin striations (striae), aggravation of infection, and other permanent skin damage (telangiectases). Other possible side effects of conventional ointments and creams are so-called steroid acne, macular or more extensive cutaneous hemorrhages, and skin ulcers in the area of application.

European published application 0,098,568, a counterpart to British published application 2,122,899, discloses a preparation for topical application that includes 0.005 to 2 weight percent of an anti-inflammatory corticoid and 1 to 50 weight percent jojoba oil.

German Patent No. 638,859 discloses a process for producing an aqueous alcohol solution that contains cholesterol and is said to be suitable for therapeutic purposes, in particular for the treatment of the scalp.

Example 6 of German Laid-Open Patent Application No. 3,526,669 discloses a moisturizing cream that has vaseline oil and cholesterol as its ingredients. Such an emulsion system is said to be usable for the production of cosmetic and pharmaceutical emulsions.

German Offenlegungsschrift (printed, unexamined application) 3,526,669, is a counterpart to British published application 2,162,439, and further discloses a water-in-oil emulsifying system comprising an alkaline earth or other metal lanolate, and a sterol, in which the sterol may be a cholesterol of β-sitosterol. Emulsions containing this emulsifying system are disclosed as being useful in cosmetic and pharmaceutical applications.

German Laid-Open Patent Application No. 3,125,710 describes a cosmetic preparation, in the form of oil-in-water dispersions among others. Example 4 relates to a treatment fluid that, among other, also contains cholesterol.

Cosmetic products that contain cholesterol dissolved in oil are also known from French Patent No. 928,337.

German Laid-Open Patent Application No. 3,713,492 discloses a concentrate for the treatment of irritated skin, which in addition to a lipid, water and glycerine, also contains cholesterol.

German Laid-Open Patent Application No. 3,319,304 discloses a medication with antineoplastic action is described that besides a lipophilic solvent also contains cholesterol.

Swiss Patent No. 143,520 describes the cosmetic properties of cholesterol, which is contained in an aqueous or aqueous-alcohol solution.

In "Pharmazeutische Technologie" [Pharmaceutical Technology], published by Sucker, Fuchs and Speiser, Stuttgart, 1978, pp. 305-310, cholesterol is mentioned as an emulsifier in dermatological products. It is also mentioned on page 659 that lanolin can be spread over the skin and has a softening effect on the horny layer of the epidermis.

Finally, the "Handbuch der Kosmetika und Riechstoffe" [Handbook of Cosmetics and Fragrances], by Janistyn, Vol. 1, Heidelberg, 1969, page 538, mentions that jojoba oil is used as a wound healing agent and as a hair oil.

The group of patients in which the aforementioned side effects occur has grown rapidly in recent years because of environmental stresses. Such patients can no longer be cured with the known pharmaceutical topical preparations, partly because of allergic reactions to the preservatives customarily employed.

SUMMARY OF THE INVENTION

It is therefore an object of the present invention to devise a highly effective ointment, free of side effects, for the treatment of dermatoses and particularly psoriasis.

This object and others to become apparent as the specification progresses, are achieved by the invention according to which briefly stated, an effective amount of cholesterol has been used for the production of a pharmaceutical compound of the topical treatment of dermatoses.

The cholesterol-containing topical ointment according to the invention has been found to be particularly effective in treating psoriasis.

The ointment according to the invention comprises from 10 to 50% by weight vaseline, 10 to 50% by weight jojoba oil, 1 to 10% by weight cholesterol, 1 to 10% by weight beeswax or spermaceti or a spermaceti substitute, as well as 10 to 40% by weight water.

Vaseline is a mixture of soft to ointment-like solid consistency of solid and liquid petroleum hydrocarbons having a melting range between 35° and 60° Celsius. Yellow vaseline (vaselinum flavum) and bleached white vaseline (vaselinum album) are the customary commercial forms. The white, highly purified vaseline preferred here serves as an inert vehicle in the ointment.

The oil obtained from the jojoba plant together with the vaseline also serves as a vehicle but additionally has a therapeutic effect.

The essential pharmaceutically active substance is cholesterol, which is contained in the ointment in a relatively high proportion by weight. Cholesterol as a pharmaceutically active ingredient in a topical ointment for the treatment of dermatoses, in particular psoriasis, cholesterol is not known from the published prior art discussed above.

Chemically, cholesterol belongs to the steroids, but it does not have the anti-inflammatory activity of the adrenocortical hormones, which are derived from steroids. As a result, the well-known side effects of steroids need not be tolerated. Cholesterol is preferably used in a highly pure form (cholesterinum purissimum). For preparing the ointment, cholesterol obtained from lanolin can be used in the form of a crystallized powder.

White or yellow beeswax, or also spermaceti or a spermaceti substitute, and the percentage of water (aqua destillata) influence the consistency of a readily spreadable ointment. Spermaceti (cetaceum) is a white waxlike composition that is obtained from the head cavity of the sperm whale and chemically primarily comprises cetyl palmitate. Today, instead of genuine spermaceti, a synthetically prepared spermaceti substitute having the same chemical composition is usually employed.

As a lipid, the cholesterol contained in the ointment of the composition according to the invention has an emulsifying effect. Since it is a substance similar to those produced by the body, it does not meet with tolerance problems or cause allergic reactions when applied to diseased skin surfaces. The ointment according to the invention is thus the ideal alternative preparation for the treatment of dermatoses in patients unable to tolerate any of the conventional preparations on their skin. For patients who can no longer be treated with the conventional preparations, the ointment proposed provides a new perspective. For a growing number of patients, the ointment according to the invention is the only known way of attaining therapeutic results without side effects.

An ointment that comprises from 20 to 40% by weight vaseline, 25 to 45% by weight jojoba oil, 2 to 6% by weight cholesterol, 2 to 8% by weight beeswax, spermaceti or a spermaceti substitute, and 15 to 30% by weight water has proved to be particularly effective in treating psoriasis. In particular, a composition of from 25 to 35% by weight vaseline, 35 to 42% by weight jojoba oil, 3 to 5% by weight cholesterol, 4 to 7% by weight beeswax, spermaceti or a spermaceti substitute, and 20 to 25% by weight water is preferred.

The ointment is prepared in the usual manner by carefully mixing the ingredients at an elevated temperature. Preferably, vaseline, jojoba oil, cholesterol and beeswax are heated together to approximately 75° C. With careful agitation, a low-viscosity, two-phase mixture results. Depending on the consistency desired, a suitable quantity of distilled water is added. The ensuing cooling to ambient temperature should take place under continued agitation. Suitable devices for this manufacturing process are known and include heat exchangers and mixers.

The ointment of the proposed composition need not have any preservatives added. Adequate shelf life is attainable, for example, merely by vacuum packing. For a longer shelf life, however, conventional preservatives may be added.

The examples below explain the composition of the ointment according to the invention:

EXAMPLE 1

| vaseline | 32% by weight |
| jojoba oil | 38% by weight |
| cholesterol | 3% by weight |
| yellow beeswax | 5% by weight |
| distilled water | 22% by weight |

EXAMPLE 2

| vaseline | 30% by weight |
| jojoba oil | 40% by weight |
| cholesterol | 4% by weight |
| spermaceti substitute | 6% by weight |
| distilled water | 20% by weight |

The ointment according to the above Example 1 was tested in trials, performed under medical supervision, of patients suffering from chronic, therapy-resistant psoriasis.

In a first clinical trial, a total of 27 patients were treated. In each case, one half of the body of the patient was treated at the affected skin sites with ointment of the composition disclosed in Example 1, while the other half of the body was treated with an ointment containing salicyl. The ointment was applied twice a day. The success of the treatment was checked by the trial supervisor after one, two and three weeks. Of the 27 patients treated, 24 were already free of symptoms after only one or two weeks. For the other three patients, although some effect was evident, complete healing of the skin changes did not occur.

A total of 21 patients took part in a second trial. Twelve of them were treated with a topical ointment according to Example 1, while the other nine patients were treated with a topical ointment without the cholesterol additive, but otherwise of the same composition. The nine psoriasis patients treated exhibited no changes whatever in the condition of their skin at the end of the three-week trial period. In the other twelve patients treated with the ointment according to the invention, the psoriasis efflorescences disappeared in ten cases.

While serious side effects such as atrophy, telangiectases, thinning of the skin and striae in the vicinity of the affected skin sites occur in many patients treated for a longer period of time with ointments containing steroids, such negative concomitant phenomena were not found in patients treated with the ointment according to the invention. The patient's statements of their subjective impressions, recorded during the trials, were equally positive.

I claim:

1. A composition for treating psoriasis, comprising:
   a) 10 to 50% by weight petroleum jelly;
   b) 10 to 50% by weight jojoba oil;
   c) 1 to 10% by weight cholesterol;
   d) 1 to 10% by weight of a compound selected from the group consisting of beeswax, spermaceti, and a spermaceti substitute; and
   e) 10 to 40% by weight water,
said composition adapted to be applied to the skin of an animal in an amount effective to treat said psoriasis.

2. The composition as defined in claim 1, wherein said composition comprises:
   a) 20 to 40% by weight petroleum jelly;
   b) 25 to 45% by weight jojoba oil;
   c) 2 to 6% by weight cholesterol;
   d) 2 to 8% by weight of a compound selected from the group consisting of beeswax, spermaceti, and a spermaceti substitute; and
   e) 15 to 30% by weight water.

3. The composition as defined in claim 1, wherein said composition comprises:
   a) 25 to 35% by weight petroleum jelly;
   b) 35 to 42% by weight jojoba oil;
   c) 3 to 5% by weight cholesterol;
   d) 4 to 7% by weight of a compound selected from the group consisting of beeswax, spermaceti, and a spermaceti substitute; and
   e) 20 to 25% by weight water.

4. A method of treating psoriasis comprising topically applying to the skin of an animal a composition comprising cholesterol in an amount effective to treat said dermatosis.

5. The method as defined in claim 4, wherein said composition comprises:
   a) 10 to 50% by weight petroleum jelly;
   b) 10 to 50% by weight jojoba oil;
   c) 1 to 10% by weight cholesterol;

d) 1 to 10% by weight of a compound selected from the group consisting of beeswax, spermaceti, and a spermaceti substitute; and e) 10 to 40% by weight water.

6. The method as defined in claim 5, wherein said composition comprises:

a) 20 to 40% by weight petroleum jelly;

b) 25 to 45% by weight jojoba oil;

c) 2 to 6% by weight cholesterol;

d) 2 to 8% by weight of a compound selected from the group consisting of beeswax, spermaceti, and a spermaceti substitute; and e) 15 to 30% by weight water.

7. The method as defined in claim 5, wherein said composition comprises:

a) 25 to 35% by weight petroleum jelly;

b) 35 to 42% by weight jojoba oil;

c) 3 to 5% by weight cholesterol;

d) 4 to 7% by weight of a compound selected from the group consisting of beeswax, spermaceti, and a spermaceti substitute; and e) 20 to 25% by weight water.

* * * * *